(12) United States Patent
Uchiyama et al.

(10) Patent No.: US 10,512,767 B2
(45) Date of Patent: Dec. 24, 2019

(54) HEMOSTATIC CONNECTOR (71) Applicant: GOODMAN CO., LTD., Nagoya-shi, Aichi-ken (JP)

(72) Inventors: Seijiro Uchiyama, Seto (JP); Kei Izawa, Seto (JP); Satoshi Nunome, Nagoya (JP); Yugo Nishimura, Nagoya (JP); Akifumi Ishiguro, Seto (JP)

(73) Assignee: GOODMAN CO., LTD., Nagoya-shi, Aichi-ken (JP)

(*) Notice: Subject to any disclaimer, the term of this patent is extended or adjusted under 35 U.S.C. 154(b) by 71 days.

(21) Appl. No.: 15/829,184

(22) Filed: Dec. 1, 2017

(65) Prior Publication Data
US 2018/0085567 A1 Mar. 29, 2018

Related U.S. Application Data (63) Continuation-in-part of application No. PCT/JP2016/065523, filed on May 26, 2016.

(30) Foreign Application Priority Data

Jun. 3, 2015 (JP) ................. 2015-112940

(51) Int. Cl.
*A61M 39/06* (2006.01)
*A61M 39/10* (2006.01)
*A61B 17/12* (2006.01)

(52) U.S. Cl.
CPC ... *A61M 39/0693* (2013.01); *A61B 17/12013* (2013.01); *A61M 39/06* (2013.01);
(Continued)

(58) Field of Classification Search
CPC .. A61M 39/0693; A61M 39/06; A61M 39/10; A61M 2039/062; A61B 17/12013; A61B 2017/12004
See application file for complete search history.

(56) References Cited

U.S. PATENT DOCUMENTS 10,238,855 B2 3/2019 Weber et al.
2004/0260243 A1 12/2004 Rickerd
(Continued)

FOREIGN PATENT DOCUMENTS

CN 202096597 U 1/2012
JP 2008-000450 A 1/2008
(Continued)

OTHER PUBLICATIONS

Dec. 19, 2018—(EP) Extended Search Report—App 16803179.7.
(Continued)

*Primary Examiner* — Amber R Stiles
(74) *Attorney, Agent, or Firm* — Banner & Witcoff, Ltd.

(57) ABSTRACT

A hemostatic connector includes an insertion hole, a hemostatic member, a connector main body part, and a coupling pipe part. The insertion hole is configured such that an introduction member is inserted through the insertion hole. The hemostatic member is configured to block a gap between a peripheral surface of the insertion hole and the introduction member. The hemostatic member is provided in the connector main body part. The coupling pipe part is configured to be coupled to a hub of a sheath introducer. The coupling pipe part is configured to be coupled to the hub in a state in which the coupling pipe part penetrates a hemostatic valve provided in an internal hole of the hub when the coupling pipe part is inserted into the internal hole. The connector main body part and the coupling pipe part are configured to be inseparable.

4 Claims, 8 Drawing Sheets

(52) U.S. Cl.
CPC ... *A61M 39/10* (2013.01); *A61B 2017/12004* (2013.01); *A61M 2039/062* (2013.01)

(56) References Cited

U.S. PATENT DOCUMENTS

2010/0280463 A1* 11/2010 Murayama ............ A61M 39/06
604/284
2016/0287857 A1    10/2016 Weber et al.

FOREIGN PATENT DOCUMENTS

| JP | 2014-195630 A | 10/2014 | |
|---|---|---|---|
| JP | 2014-212908 A | 11/2014 | |
| WO | 2009-091018 A1 | 7/2009 | |
| WO | 2014/175021 A1 | 10/2014 | |
| WO | WO-2014175021 A1 * | 10/2014 | ............ A61M 39/06 |
| WO | 2015067359 A1 | 5/2015 | |

OTHER PUBLICATIONS

Dec. 5, 2017—(WO) IPRP—App PCT/JP2016/065523—Eng Translation.
Aug. 22, 2016—International Search Report—Intl App PCT/JP2016/065523.
May 7, 2019—(JP) Notification of Reason for Rejection—App 2015-112940.
Oct. 29, 2019—(CN) First Office Action—App 201680031113.5.

* cited by examiner

HEMOSTATIC CONNECTOR

CROSS-REFERENCE TO RELATED APPLICATION

This application is a continuation-in-part of International Application No. PCT/JP2016/065523, filed May 26, 2016, which claims priority from Japanese Patent Application No. 2015-112940, filed on Jun. 3, 2015. The disclosure of the foregoing application is hereby incorporated by reference in its entirety.

BACKGROUND

The present disclosure relates to a hemostatic connector.

In general, when an introduction member, such as a catheter or the like, is introduced into a blood vessel as far as a treatment target location during the treatment of heart disease or the like, first, a sheath introducer is inserted into the blood vessel by being caused to pierce the blood vessel. After that, a guiding catheter is introduced into the blood vessel through the interior of the sheath introducer. A Y connector is attached to a base end part of the guiding catheter. The introduction member is inserted into the guiding catheter through the Y connector. Then, in that inserted state, the introduction member is introduced as far as the treatment target location inside the blood vessel. Further, when introducing the introduction member into the blood vessel, blood is stopped by a hemostatic valve provided inside the Y connector.

Here, in recent years, when the treatment target location is in a comparatively close position to a location at which the blood vessel is pierced by the sheath introducer or the like, the introduction member is introduced as far as the treatment target location without using the guiding catheter. In other words, after the sheath introducer has been inserted into the blood vessel, the introduction member is introduced into the blood vessel through the inside of the sheath introducer. In this case, since there is no need to use the guiding catheter, an operation to introduce the introduction member into the blood vessel can be swiftly performed.

Here, when the introduction member is introduced into the blood vessel via the interior of the sheath introducer, the introduction member is introduced in a state in which the introduction member penetrates a hemostatic valve provided inside a hub of the sheath introducer. However, normally, the guiding catheter that has a larger diameter than the introduction member is inserted through the hemostatic valve inside the hub, and thus, when the introduction member is inserted, there is a risk of insufficient blood stoppage and that blood leakage may occur.

Here, as a measure to deal with this problem, a configuration in which a Y connector is coupled to the base end side of the hub via an adaptor is known. According to this configuration, the introduction member is inserted into the sheath introducer through the interior of the Y connector and the interior of the adaptor, and the introduction member is introduced into the blood vessel in the inserted state. In this case, when introducing the introduction member into the blood vessel, blood stoppage is performed using a hemostatic valve inside the Y connector, specifically, a hemostatic valve that has a superior hemostatic performance compared to the hemostatic valve inside the hub. As a result, when introducing the introduction member into the blood vessel through the inside of the sheath introducer, the leakage of blood can be suppressed.

SUMMARY

Here, in the above-described configuration, when introducing the introduction member into the blood vessel, as well as coupling the adaptor to the base end side of the hub, an operation arises to couple the Y connector to the base end side of the adaptor. However, when introducing the introduction member into the blood vessel, it is troublesome to perform a plurality of coupling operations, and moreover, there is a risk that it may be difficult to rapidly introduce the introduction member into the blood vessel.

Various embodiments of the broad principles derived herein provide a hemostatic connector capable of favorably performing an introduction operation while suppressing the leakage of blood, when introducing an introduction member into a blood vessel through the interior of a sheath introducer.

Embodiments provide a hemostatic connector that includes an insertion hole, a hemostatic member, a connector main body part, and a coupling pipe part. The insertion hole is configured such that an introduction member that is introduced into a human body is inserted through the insertion hole. The hemostatic member is configured to block a gap between a peripheral surface of the insertion hole and the introduction member. The hemostatic member is provided in the connector main body part. The connector main body part configures a first passage that is a portion of the insertion hole. The coupling pipe part is configured to be coupled to a hub of a sheath introducer. The coupling pipe part configures a second passage that is a portion of the insertion hole different to the first passage. The coupling pipe part is configured to be inserted into an internal hole of the hub from a base end side of the hub. The coupling pipe part is configured to be coupled to the hub in a state in which the coupling pipe part penetrates a hemostatic valve provided in the internal hole when the coupling pipe part is inserted into the internal hole. The connector main body part and the coupling pipe part are configured to be inseparable.

BRIEF DESCRIPTION OF THE DRAWINGS

Embodiments will be described below in detail with reference to the accompanying drawings in which.

DETAILED DESCRIPTION

Figure 1:
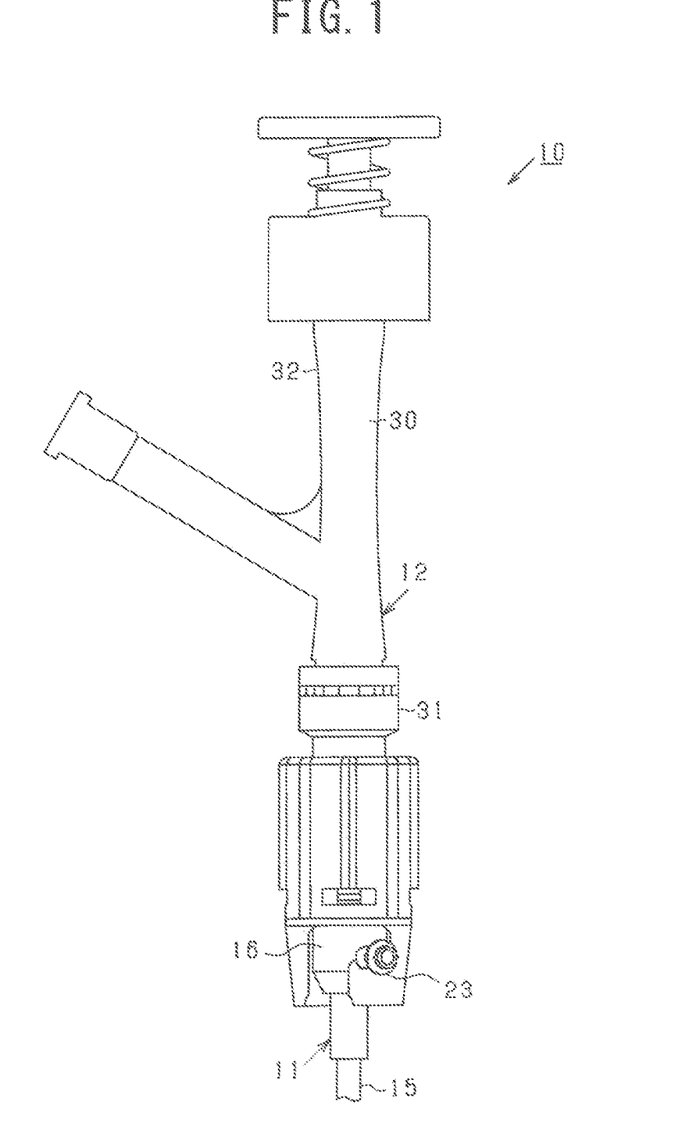
FIG. 1 is a front view showing a configuration of a sheath introducer assembly.
Figures 2A, 2B:
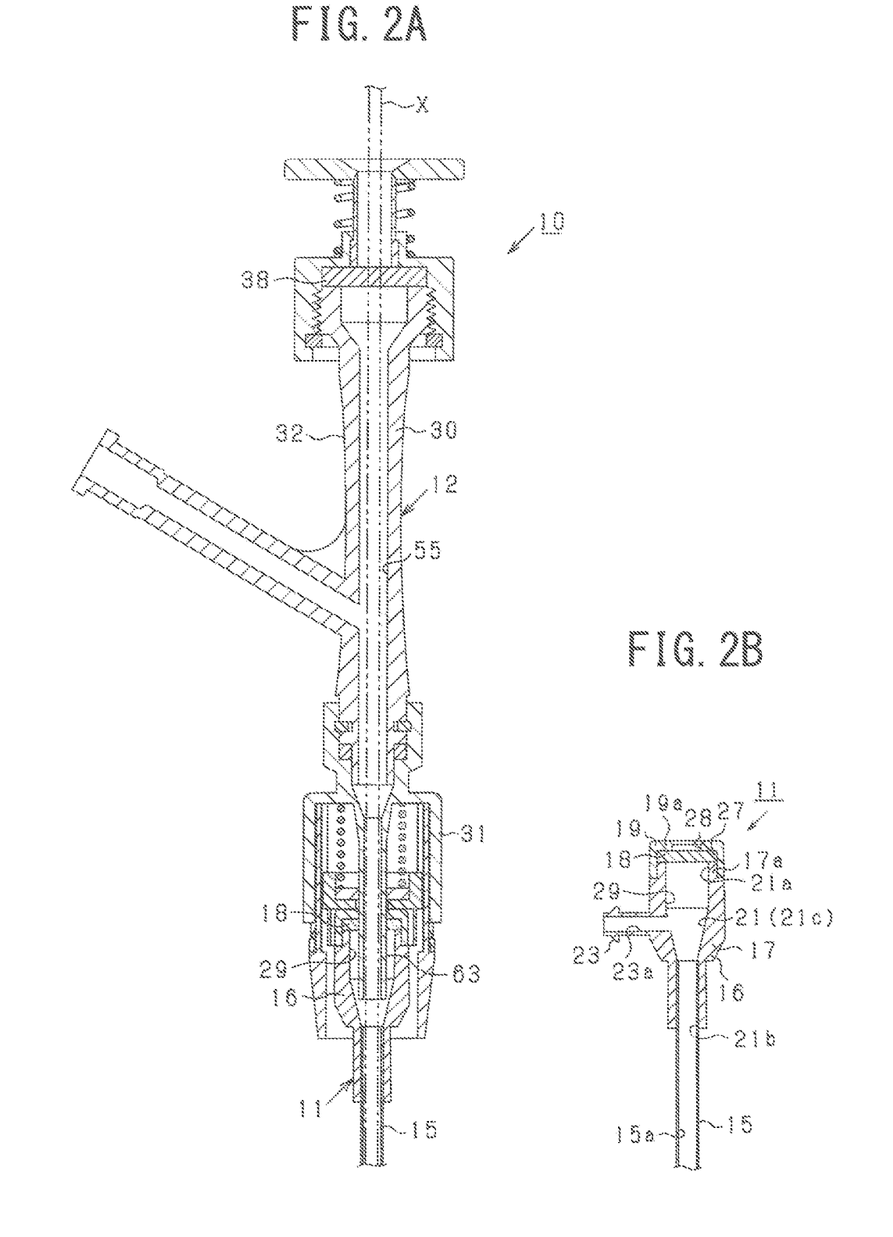
FIG. 2A is a longitudinal cross-sectional view showing the configuration of the sheath introducer assembly.
FIG. 2B is a longitudinal cross-sectional view showing a sheath introducer.

Hereinafter, an embodiment embodying the present disclosure will be explained with reference to the drawings. In the present embodiment, a sheath introducer assembly configured having a sheath introducer is embodied. FIG. 1 is a front view showing the configuration of the sheath introducer assembly. FIG. 2A is a longitudinal cross-sectional view showing the configuration of the sheath introducer assembly. FIG. 2B is a longitudinal cross-sectional view showing the sheath introducer. Note that FIGS. 2A and 2B are longitudinal cross-sectional views cut along respectively difference surfaces. In FIGS. 1, 2A, and 2B, the upward direction and the downward direction are, respectively, a base end side and a leading end side of a sheath introducer assembly 10.

As shown in FIG. 1 and FIG. 2A, the sheath introducer assembly 10 is provided with a sheath introducer 11, and a hemostatic connector 12 coupled with a hub 16 of the sheath introducer 11.

The sheath introducer 11 is inserted into a blood vessel by piercing the blood vessel. As shown in FIG. 2B, the sheath introducer 11 is provided with a sheath tube 15, and the hub 16 that is attached to the base end part (a proximal end part) of the sheath tube 15. The sheath tube 15 is formed in a tubular shape from a flexible resin material, and has a lumen 15a into or through which an introduction member X of a balloon catheter or the like can be inserted or passed.

The hub 16 has a main body part 17, a hemostatic valve 18, and a cap 19. The main body part 17 is formed in a circular pipe (circular cylindrical) shape from a resin material such as polyethylene, and has a pipe bore 21 that extends internally along the whole of the main body part 17 in an axial line direction. The pipe bore 21 has a large diameter region 21a, a diameter reduction region 21c, and a small diameter region 21b, in that order from the base end side toward the leading end side. A hole diameter of the large diameter region 21a is larger than a hole diameter of the small diameter region 21b. In the diameter reduction region 21c, the hole diameter becomes smaller from the large diameter region 21a toward the small diameter region 21b.

The base end part of the sheath tube 15 is inserted into the leading end part (the small diameter region 21b) of the pipe bore 21. In that inserted state, the sheath tube 15 is fixed to the main body part 17 by thermal welding, an adhesive or the like. In this way, the sheath tube 15 and the main body part 17 (namely, the hub 16) are coupled together and the lumen 15a of the sheath tube 15 and the pipe bore 21 of the main body part 17 are communicated with each other.

A branch pipe part 23 is provided so as to protrude from the outer peripheral surface of the main body part 17. The branch pipe part 23 protrudes in a direction that is orthogonal to (intersects) the axial line direction, from an intermediate portion of the main body part 17 in the axial line direction. In the axial line direction of the pipe bore 21, the branch pipe part 23 is positioned further to the base end side than the small diameter region 21b, and more specifically, is in the same position as the diameter reduction region 21c.

A pipe bore 23a that is communicated with the pipe bore 21 is formed in the interior of the branch pipe part 23. Although not shown in the drawings, a conduit is connected to the branch pipe part 23, and various devices can be connected to the conduit. For example, a liquid solution supply unit that supplies a liquid solution such as a contrast medium, is connected to the conduit. In this case, the liquid solution is supplied into the human body from the liquid solution supply unit via the pipe bores 21 and 23a. Further, there is a case in which a blood pressure monitor that monitors blood pressure is connected to the conduit. In this case, the pressure inside the blood vessel is monitored via the pipe bores 21 and 23a.

A diameter reduction part 17a, whose outer diameter is made smaller, is formed in the base end part of the main body part 17. The hemostatic valve 18 is provided on the base end side of the diameter reduction part 17a. The hemostatic valve 18 is formed in a circular plate shape from an elastic material, such as silicone rubber or the like, and is provided so as to block an opening on the base end side of the pipe bore 21. A slit (not shown in the drawings) is formed in the hemostatic valve 18, and the slit penetrates the hemostatic valve 18 in the thickness direction of the hemostatic valve 18. The slit is cross-shaped, for example, and is in a constantly closed state due to the elasticity of the hemostatic valve 18. However, the slit may be formed in a chosen shape, such as a straight line or the like. Note that the hemostatic valve 18 is positioned further to the base end side than the branch pipe part 23.

The cap 19 is formed in a bottomed circular cylindrical shape from the same resin material as the main body part 17. The cap 19 includes a housing recessed part 27, and the hemostatic valve 18 is housed inside the housing recessed part 27. In a state in which the hemostatic valve 18 is housed inside the housing recessed part 27, the cap 19 is fixed to the main body part 17, such that the cap 19 is caused to cover the diameter reduction part 17a. In this way, the hemostatic valve 18 is disposed between a bottom part 19a of the cap 19 and the diameter reduction part 17a. Further, a through hole 28 is formed in a central portion of the bottom part 19a of the cap 19 so as to penetrate the bottom part 19a in the thickness direction. In this case, an internal passage 29 of the hub 16 is configured by the pipe bore 21 of the main body part 17, the housing recessed part 27, and the through hole 28, and the introduction member X is inserted through the internal passage 29.

Figure 3:
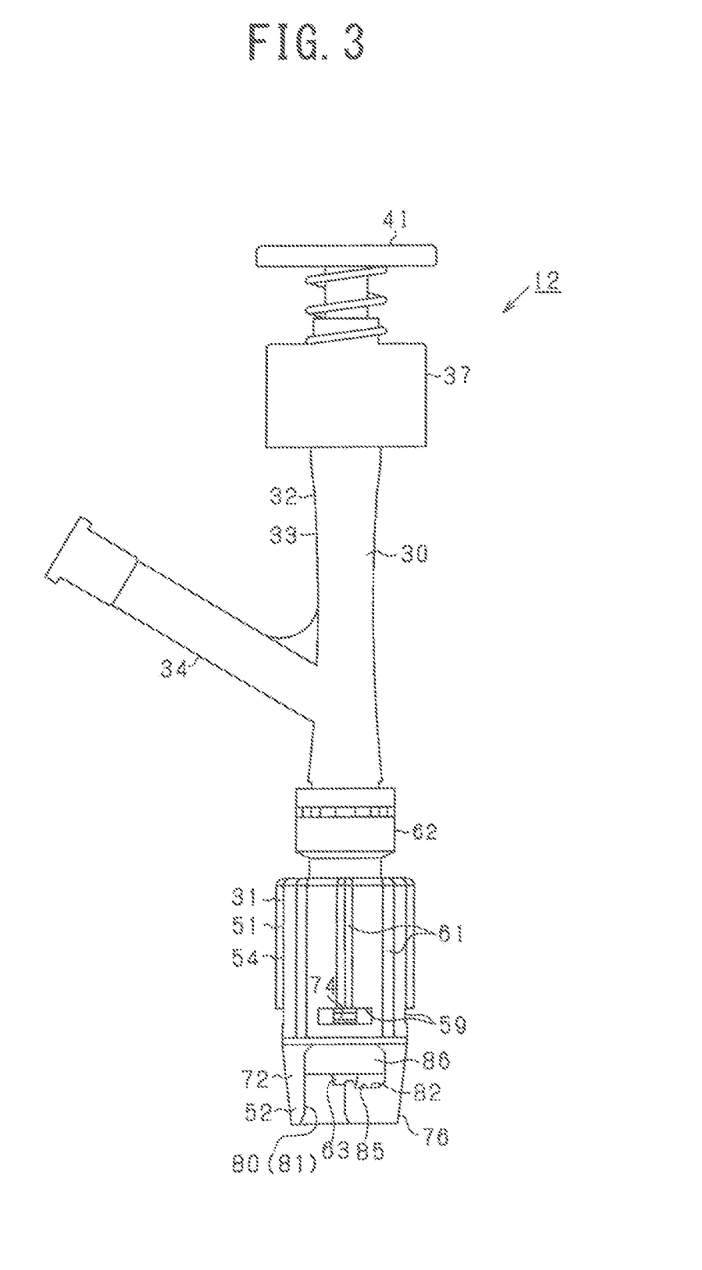
FIG. 3 is a front view showing a configuration of a hemostatic connector.
Figure 4:
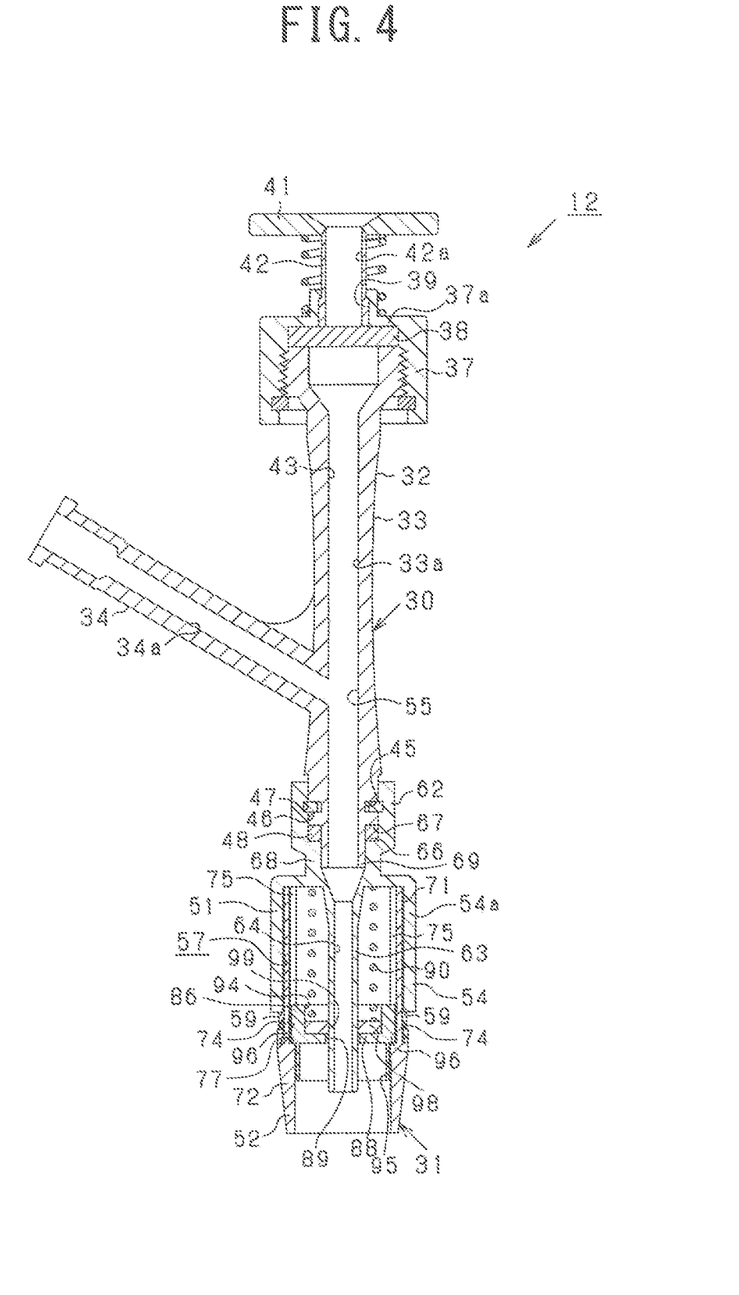
FIG. 4 is a longitudinal cross-sectional view showing the configuration of the hemostatic connector.

Next, the configuration of the hemostatic connector 12 will be explained on the basis of FIG. 3 and FIG. 4. FIG. 3 is a front view showing the configuration of the hemostatic connector 12. FIG. 4 is a longitudinal cross-sectional view showing the configuration of the hemostatic connector 12. In FIG. 3 and FIG. 4, the upward direction and the downward direction are, respectively, the base end side and the leading end side of the hemostatic connector 12.

As shown in FIG. 3 and FIG. 4, the hemostatic connector 12 is provided with a Y connector part 30 as a connector main body part, and a hub coupling part 31 which can be coupled to the hub 16 of the sheath introducer 11. The Y connector part 30 is provided with a main body part 32 formed in a Y-shape, a screw 37, and an opener 41. The main body part 32 is formed from a transparent synthetic resin material, such as a polycarbonate or the like. The main body part 32 includes a main pipe part 33, and a branch pipe part 34 that is provided branching from the main pipe part 33. A pipe bore 33a is formed in the interior of the main pipe part 33, and a pipe bore 34a is formed in the interior of the branch pipe part 34. The pipe bores 33a and 34a are communicated with each other.

The screw 37 is attached to the base end part of the main pipe part 33. The screw 37 is formed in a bottomed circular cylindrical shape, and an inside space thereof is open to the leading end side. The base end part of the main pipe part 33 is inserted into the inside space of the screw 37, and the inserted base end part is screwed into the inner peripheral surface of the screw 37. Further, a through hole 39 is formed in a bottom part 37a of the screw 37 so as to penetrate the bottom part 37a in the thickness direction.

A hemostatic valve 38 is housed in a space surrounded by the base end part of the main pipe part 33 and the screw 37. The hemostatic valve 38 has a comparatively high hemostatic performance, and has a higher hemostatic performance than the hemostatic valve 18 inside the hub 16. The hemostatic valve 38 is formed in a circular plate shape from an elastic material, such as silicone rubber or the like, and is disposed coaxially with the main pipe part 33 (the pipe bore 33a). A slit (not shown in the drawings) is formed in the hemostatic valve 38, so as to penetrate the hemostatic valve 38 in the thickness direction thereof. The slit is cross-shaped, for example, and is in a constantly closed state due to the elasticity of the hemostatic valve 38. However, the slit may be formed in a chosen shape, such as a straight line or the like.

The opener 41 is attached to the base end side of the screw 37. The opener 41 has a penetrating part 42 for penetrating the hemostatic valve 38. The penetrating part 42 is formed in a circular pipe shape and has a pipe bore 42a on the inside thereof. The penetrating part 42 is provided so as to be inserted through the through hole 39 of the bottom part 37a of the screw 37, and the pipe bore 42a and the pipe bore 33a of the main pipe part 33 are communicated with each other via the inside space of the screw 37. In this case, an internal passage 43 of the Y connector part 30 is configured by the pipe bores 33a and 42a and the inside space of the screw 37 that mutually connects the pipe bores 33a and 42a. In other words, the internal passage 43 is a hole that extends from the base end as far as the leading end of the Y connector part 30.

It should be noted that a normal Y connector that is distributed on the market includes a Y connector main body part with a built-in hemostatic valve, and a rotator that is attached to the leading end part of the Y connector main body part. The rotator is a coupling tool for coupling another medical device. The rotator is rotatably attached to the Y connector main body part. In the present embodiment, the Y connector main body part of the general Y connector is used as the Y connector part 30 (the connector main body part). Specifically, the Y connector part 30 is configured by a structural component (the Y connector main body part) of the general Y connector.

Figure 5A:
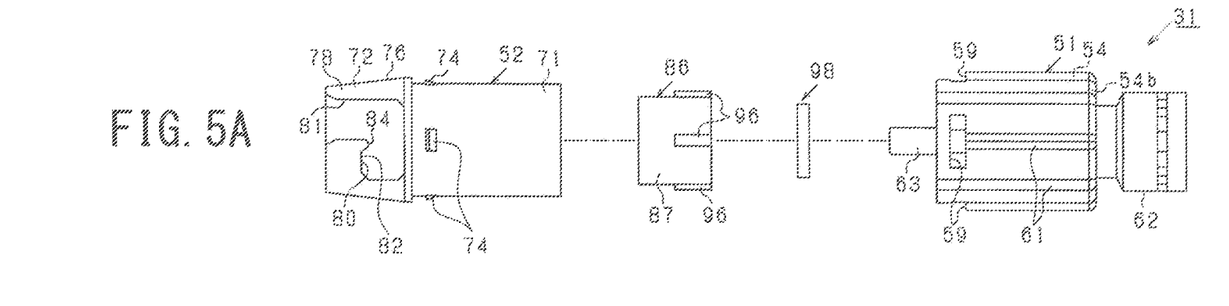
FIG. 5A is an exploded front view showing a configuration of a hub coupling part.
Figure 5B:
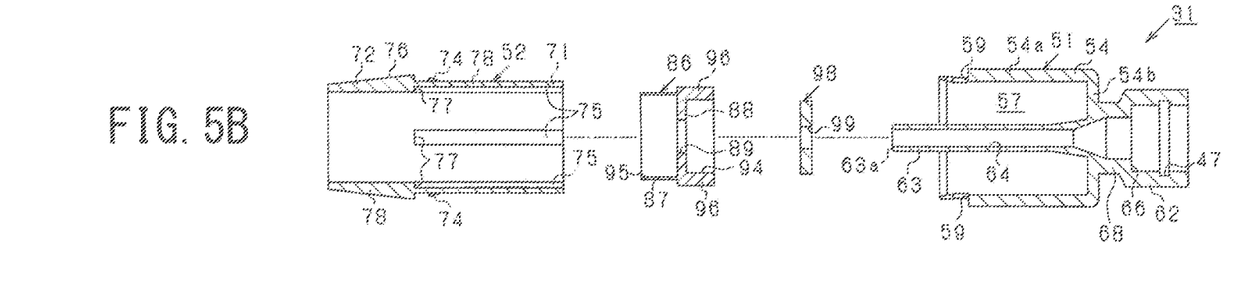
FIG. 5B is an exploded longitudinal cross-sectional view showing the configuration of the hub coupling part.

The hub coupling part 31 will be explained with reference to FIGS. 5A and 5B in addition to FIG. 3 and FIG. 4. FIG. 5A is an exploded front view of the configuration of the hub coupling part 31, and FIG. 5B is an exploded longitudinal cross-sectional view of the hub coupling part 31. The upward direction and the downward direction in FIGS. 5A and 5B are, respectively, the base end side and the leading end side of the hub coupling part 31.

As shown in FIGS. 3, 4, 5A, and 5B, the hub coupling part 31 is inseparably (non-detachably) attached to the leading end part of the main pipe part 33 of the Y connector part 30 (the main body part 32). Specifically, in the present embodiment, the hub coupling part 31 is attached to a portion to which the rotator is attached in the case of the general Y connector. The hub coupling part 31 is provided with a first body 51 and a second body 52. The first body 51 and the second body 52 are joined to each other. A body main body of the hub coupling part 31 is configured by the bodies 51 and 52. Further, the bodies 51 and 52 are both formed from the same resin material, and both of the bodies 51 and 52 are formed, for example, from a transparent resin material such as a polycarbonate or the like.

The first body 51 is provided with a cylindrical part 54. The cylindrical part 54 is a bottomed circular cylindrical part. The cylindrical part 54 includes a housing recessed part 57 and the second body 52 is housed inside the housing recessed part 57. The cylindrical part 54 includes a peripheral wall part 54a and a bottom plate part 54b. The peripheral wall part 54a surrounds the housing recessed part 57. The bottom plate part 54b defines a bottom surface of the housing recessed part 57. A plurality (four in the present embodiment) of holes 59 that penetrate in the thickness direction are formed in the leading end side of the peripheral wall part 54a. Each of the holes 59 has a rectangular shape. The plurality of holes 59 are arranged at equal intervals (more specifically, at 90 degree intervals) in the peripheral direction of the peripheral wall part 54a. Note that, in the present embodiment, of the respective holes 59, a predetermined two of the holes 59 that face each other are long holes that are longer in the peripheral direction than the two other holes 59.

A plurality of ribs 61 that extend in the axial line direction are provided on the outer peripheral surface of the cylindrical part 54 (the peripheral wall part 54a), at predetermined intervals (more specifically, at equal intervals) in the peripheral direction. The strength of the cylindrical part 54 is increased by the plurality of ribs 61. Further, since the outer peripheral surface of the cylindrical part 54 becomes the outer peripheral surface of the hub coupling part 31, the cylindrical part 54 is held by hand and a coupling operation is performed when the hemostatic connector 12 (the hub coupling part 31) is coupled to the hub 16 of the sheath introducer 11. By providing the ribs 61, at the time of this coupling operation, it is possible to suppress the occurrence of a failure due to slipping of the hand.

A first pipe part 62, which extends from the bottom plate part 54b of the cylindrical part 54 to the base end side, and a second pipe part 63, which extends from the bottom plate part 54b to the leading end side, are provided on the first body 51. Both of the pipe parts 62 and 63 are formed in a cylindrical pipe shape that extends in the axial line direction, and are positioned to be mutually coaxial. Further, each of the pipe parts 62 and 63 is disposed at a central portion of the bottom plate part 54b.

A pipe bore 64, which extends across both the pipe parts 62 and 63, is provided in the first pipe part 62 and the second pipe part 63. The pipe bore 64 is formed so as to penetrate each of the first pipe part 62, the bottom plate part 54b, and the second pipe part 63 in the axial line direction. Thus, the pipe bore 64 is open to the outside at the base end of the first pipe part 62 and the leading end of the second pipe part 63, respectively.

Both the inner diameter and the outer diameter of the first pipe part 62 are larger than those of the second pipe part 63. The first pipe part 62 is coupled to the leading end part of the main pipe part 33 of the Y connector part 30 (the main body part 32). The main pipe part 33 is inserted into the pipe bore 64 of the first pipe part 62 from the base end side. The pipe parts 33 and 62 are coupled together in a state in which the main pipe part 33 is inserted into the pipe bore 64.

A coupled configuration of the main pipe part 33 and the first pipe part 62 will be explained in detail. An annular groove part 45 is formed in the outer peripheral surface of the leading end part of the main pipe part 33. An O ring 46 (an annular elastic member) made from a rubber material is disposed in the groove part 45. An annular groove part 47 is formed along the groove portion 45, in the inner peripheral surface of the first pipe part 62. A part of the O ring 46 enters into the groove part 47. The O ring 46 is disposed so as to straddle between the groove parts 45 and 47 of the main pipe part 33 and the first pipe part 62. In this way, the O ring 46 functions as a locking member that inhibits the main pipe part 33 from slipping out from the pipe bore 64 of the first pipe part 62. Due to this locking function, the first pipe part 62 and the main pipe part 33 are coupled together in a mutually inseparable (non-detachable) state. In this way, the first body 51, namely, the hub coupling part 31, is attached to the main body part 32 (the Y connector part 30) in a non-detachable (inseparable) state.

In addition, the first pipe part 62 is coupled to the main pipe part 33 so as to be able to rotate around the axial line of the main pipe part 33 (in other words, around the axial line of the second pipe part 63). In this way, the hub coupling part 31 is attached to the main body part 32 so as to be able to rotate around the aforementioned axial line.

In a state in which the first pipe part 62 is coupled to the main pipe part 33, the pipe bore 64 of the hub coupling part 31 and the pipe bore 33a of the main pipe part 33 (namely, the internal passage 43 of the Y connector part 30) are communicated with each other. In this case, the internal passage 55 of the hemostatic connector 12 is configured by the pipe bore 64 of the hub coupling part 31 and the internal passage 43 of the Y connector part 30.

A seal member 48 is disposed at a coupling portion between the first pipe part 62 and the main pipe part 33. The seal member 48 is provided in order to suppress leakage of blood from the coupling portion between the first pipe part 62 and the main pipe part 33. The seal member 48 is formed in an annular shape from an elastic material such as rubber or the like. The seal member 48 is disposed between the inner peripheral surface of the first pipe part 62 and the outer peripheral surface of the main pipe part 33. An arrangement configuration of the seal member 48 will be explained specifically. A step is formed in the inner peripheral surface of the first pipe part 62, further to the leading end side than the groove part 47. The inner diameter further to the leading end side than a step part 66 is smaller than the inner diameter further to the base end side than the step part 66. Hereinafter, a portion further to the leading end side than the step part 66 is referred to as a small diameter part 68. Meanwhile, a step is formed in the outer peripheral surface of the main pipe part 33, further to the leading end side than the groove part 45. An external shape further to the leading end side than a step part 67 is smaller than an external shape further to the base end side of the step part 67. Hereinafter, a portion further to the leading end side than the step part 67 is referred to as a small diameter part 69. The small diameter part 69 of the main pipe part 33 is inserted inside the small diameter part 68 of the first pipe part 62. The step part 66 of the first pipe part 62 and the step part 67 of the main pipe part 33 face each other in the axial line direction, with a gap therebetween, in a state in which the small diameter part 69 is inserted inside the small diameter part 68. In this case, the seal member 48 is disposed in a state of being clamped between the step parts 66 and 67. In this way, the leakage of blood is suppressed from the coupling portion between the first pipe part 62 and the main pipe part 33.

The second pipe part 63 can be inserted, from the base end side, into the internal passage 29 of the hub 16 (specifically, the pipe bore 21 of the main body part 17). The second pipe part 63 is a coupling pipe part that can be coupled to the hub 16. The outer diameter of the second pipe part 63 is smaller than the inner diameter of the large diameter region 21a of the pipe bore 21, and is larger than the inner diameter of the small diameter region 21b. In other words, the outer diameter of the second pipe part 63 is the same as the inner diameter (of a midway position of) of the diameter reduction region 21c. Further, the second pipe part 63 extends further to the leading end side than the leading end of the cylindrical part 54. An end surface 63a on the leading end side of the second pipe part 63 forms a curved surface shape that projects toward the leading end side. More specifically, the end surface 63a on the leading end side of the second pipe part 63 forms a semi-circular shape that projects toward the leading end side.

The second body 52 is formed in a circular cylindrical shape. The second body 52 includes a housed part 71 and an extending part 72. The housed part 71 is a portion that is housed in the housing recessed part 57 of the first body 51. The extending part 72 is a portion that extends to the leading end side from the housed part 71. The outer diameter of the housed part 71 is the same as or slightly smaller than the inner diameter of the housing recessed part 57. The housed part 71 is housed in the housing recessed part 57 in a state of being positioned coaxially with the first body 51 (the cylindrical part 54).

A plurality (four in the present embodiment) of protrusions 74 are provided on the outer peripheral surface of the housed part 71, on the leading end side thereof. The protrusions 74 are arranged at equal intervals along the peripheral direction of the housed part 71. More specifically, the plurality of protrusions 74 are respectively arranged at positions corresponding to the plurality of holes 59 of the first body 51. In a state in which the housed part 71 is housed in the housing recessed part 57 of the first body 51, the protrusions 74 respectively fit into the holes 59 of the first body 51 and engage with each of the holes 59. In this way the housed part 71, namely, the second body 52, is joined to the first body 51.

A plurality (four in the present embodiment) of guide grooves 75, which extend across the whole area of the housed part 71 in the axial line direction, are formed in the inner peripheral surface of the housed part 71. The guide grooves 75 are arranged at predetermined intervals in the peripheral direction of the housed part 71. More specifically, the plurality of guide grooves 75 are arranged at equal intervals (at 90 degree intervals). A step part 77 occurs at the leading end part of each of the guide grooves 75 and the leading end of the guide groove 75 is defined by the step part 77. The guide groove 75 is open at the base end thereof.

The extending part 72 has a tapered shape with the outer diameter thereof becoming smaller from the base end part toward the leading end part, and the outer peripheral surface thereof forms a tapered surface 76. The outer diameter at the base end part of the extending part 72 is larger than the outer diameter of the housed part 71. More specifically, the outer diameter of the base end part of the extending part 72 is the same as the outer diameter of the cylindrical part 54 of the first body 51.

A guide passage 80, for guiding the branch pipe part 23 of the hub 16, is formed in a peripheral wall part 78 that configures the extending part 72. The guide passage 80 is formed so as to penetrate the peripheral wall part 78 in the thickness direction. The guide passage 80 includes a first passage part 81 and a second passage part 82. The first passage part 81 extends from the leading end to the base end side of the peripheral wall part 78. The second passage part 82 extends from the base end part of the first passage part 81 toward one side in the peripheral direction of the peripheral wall part 78. Further, a protrusion 84 that protrudes toward the second passage part 82 is provided on a passage end surface 85 on the leading end side (in the axial line direction) that defines the second passage part 82 in the peripheral wall part 78, specifically, at an end part of the passage end surface 85 close to the first passage part 81.

A movable member 86 is disposed inside the second body 52. The movable member 86 is formed from the same resin material as each of the bodies 51 and 52. The movable member 86 includes a cylindrical part 87 that is formed in a circular cylindrical shape, and a circular plate-shaped partition plate part 88 that is provided on the inside of the cylindrical part 87. The partition plate part 88 is arranged coaxially with the cylindrical part 87, and is provided so as to partition an interior space of the cylindrical part 87 in the axial line direction.

In the movable member 86, recessed parts 94 and 95 are formed on both sides of the partition plate part 88. Of the recessed parts 94 and 95, an inner diameter of the recessed part 95 is larger than that of the recessed part 94. Further, a hole 89, which causes the recessed parts 94 and 95 to be communicated with each other, is formed in a central part of the partition plate part 88.

A plurality (four in the present embodiment) of guided parts 96 are protrudingly formed on the outer peripheral surface of the cylindrical part 87. Each of the guided parts 96 extends in the axial line direction of the cylindrical part 87, and more specifically, extends from the same position as the partition plate part 88 in the same direction as far as one end on the recessed part 94 side of the cylindrical part 87. The guided parts 96 are arranged at predetermined intervals (at equal intervals) in the peripheral direction of the cylindrical part 87, and, specifically, are arranged so as to respectively correspond to the guide grooves 75 of the second body 52.

The movable member 86 is disposed inside the second body 52 in a state in which the cylindrical part 87 is positioned coaxially with the second body 52. The movable member 86 is arranged while being oriented such that the recessed part 94 is open at the base end side and the recessed part 95 is open at the leading end side, and the second pipe part 63 of the first body 51 is caused to be inserted through the hole 89 of the partition plate part 88.

The movable member 86 is provided inside the second body 52 such that the movable member 86 can move in the axial line direction of the second body 52. The guided parts 96 of the movable member 86 are respectively fitted into the guide grooves 75 of the second body 52. By the guided parts 96 moving along the guide grooves 75, the movable member 86 is guided along the guide grooves 75, namely, is guided along the axial line direction of the second body 52.

A circular plate-shaped seal member 98 is fitted into the recessed part 94 of the movable member 86. The seal member 98 is formed from an elastic material such as silicone rubber or the like, and the thickness dimension thereof is smaller than a depth dimension of the recessed part 94. The seal member 98 overlaps with the base end side surface of the partition plate part 88 of the movable member 86.

A hole 99 is formed in a central portion of the seal member 98 so as to penetrate the seal member 98 in the thickness direction. The hole 99 is communicated with the hole 89 of the partition plate part 88. The second pipe part 63 of the first body 51 is inserted through both the holes 89 and 99. In this case, a "hole through which the coupling pipe part (the second pipe part 63) can be inserted" is configured by both the holes 89 and 99. The hole diameter of the hole 99 is smaller than the hole diameter of the hole 89. More specifically, the hole diameter of the hole 99 is the same as or slightly smaller than the outer diameter of the second pipe part 63. Therefore, while the inner peripheral surface of the hole 89 is separated from the outer peripheral surface of the second pipe part 63, the inner peripheral surface of the hole 99 is in close contact with the outer peripheral surface of the second pipe part 63.

Inside the second body 52, a coil spring 90 is provided, as an urging member, on the base end side of the seal member 98 (and thus of the partition plate part 88 of the movable member 86). The coil spring 90 is disposed in a compressed state between the seal member 98 and the bottom plate part 54b of the first body 51 (the cylindrical part 54). In this case, the seal member 98 and the movable member 86 are urged to the leading end side against the first body 51 (namely, the body main body), by the urging force of the coil spring 90.

Meanwhile, of the movable member 86, the guided parts 96 are in contact with the step parts 77 of the guide grooves 75. Thus, even though the movable member 86 is being urged to the leading end side by the coil spring 90, movement any further to the leading end side is regulated. In this case, the position of the movable member 86 is an initial position of the movable member 86 (refer to FIG. 4). Note that, for convenience, the coil spring 90 is not illustrated in FIGS. 5A and 5B.

Figure 6:
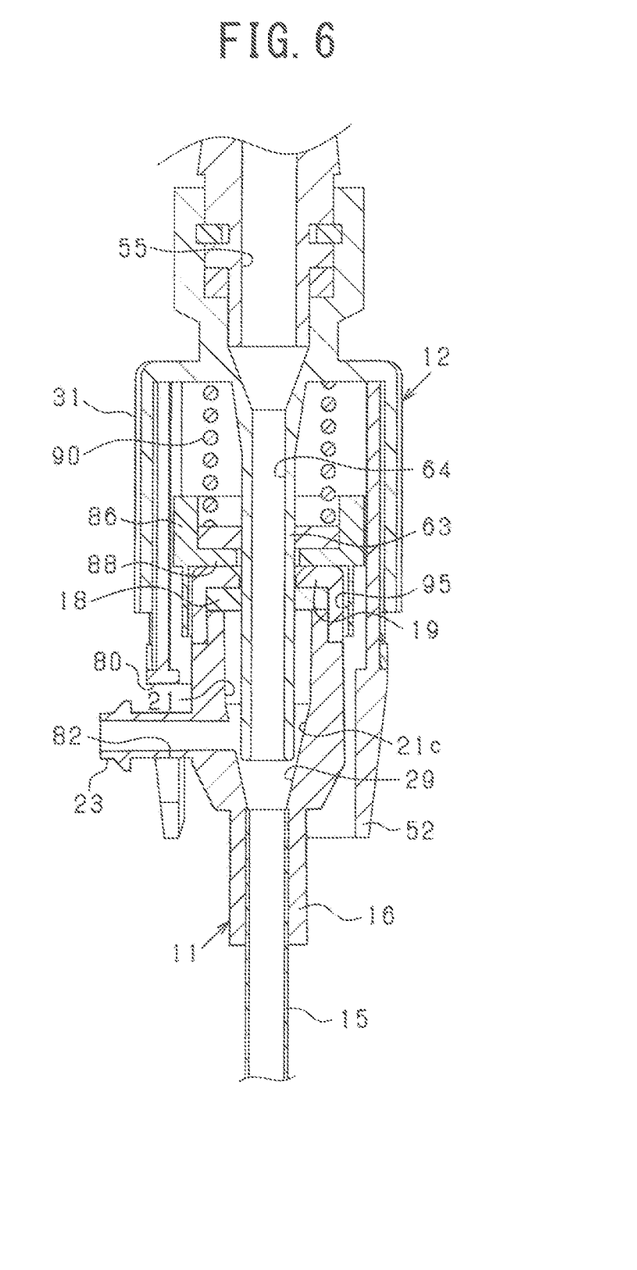
FIG. 6 is a longitudinal cross-sectional view showing a configuration of a coupling portion at which the hemostatic connector is coupled to a hub.

Next, a coupling configuration when the hemostatic connector 12 is coupled to the hub 16 of the sheath introducer 11 will be explained. FIG. 6 is a longitudinal cross-sectional view showing the configuration of the coupling portion at which the hemostatic connector 12 is coupled to the hub 16. The upward direction and the downward direction in FIG. 6 are, respectively, the base end side and the leading end side of the hemostatic connector 12.

As shown in FIG. 6, the hub coupling part 31 of the hemostatic connector 12 is coupled to the hub 16 in a state in which the hub 16 is housed inside the second body 52. The second pipe part 63 of the hub coupling part 31 is coupled to the hub 16 in a state in which the second pipe part 63 penetrates the slit of the hemostatic valve 18 of the hub 16. The pipe bore 64 (namely, the internal passage 55 of the hemostatic connector 12) of the hub coupling part 31 and the internal passage 29 of the hub 16 are communicated with each other as a result of the coupling of the second pipe part 63 and the hub 16.

In the state in which the second pipe part 63 penetrates the hemostatic valve 18, the outer peripheral surface of the second pipe part 63 and the inner peripheral surface of the slit of the hemostatic valve 18 are in close contact with each other. In this way, leakage of blood between them is suppressed. Further, the leading end part of the second pipe part 63 reaches as far as the diameter reduction region 21c of the pipe bore 21 of the hub 16, and is therefore inserted into (penetrates) the hemostatic valve 18 to a sufficient insertion depth. As a result, the hemostatic function of the hemostatic valve 18 can be deployed in a stable state.

Figure 7A:
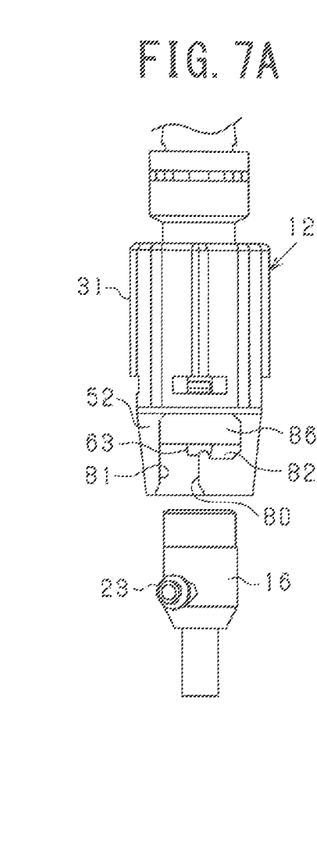
FIGS. 7A, 7B, 7C, and 7D are explanatory diagrams illustrating a flow when coupling the hemostatic connector to the hub.
Figure 7B:
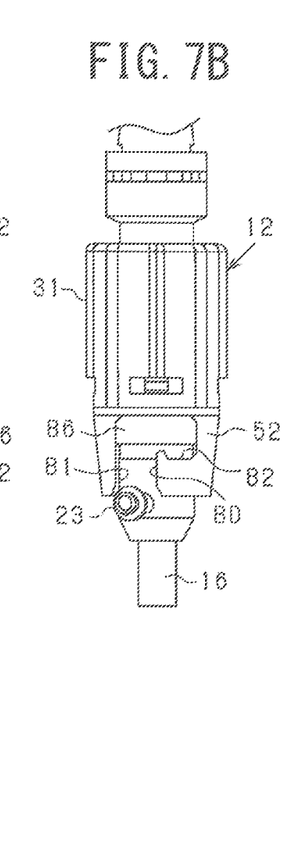
Figures 7C, 7D:
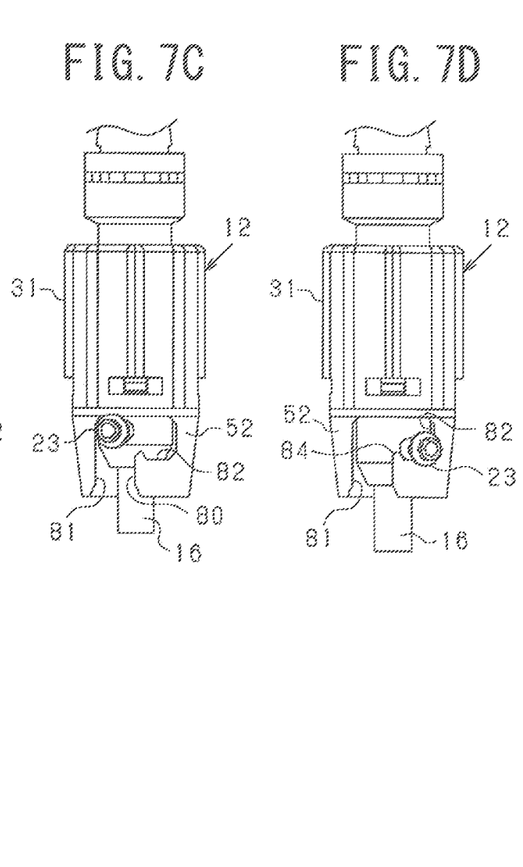

In the state in which the second pipe part 63 (the hub coupling part 31) is coupled to the hub 16, the branch pipe part 23 of the hub 16 is positioned at the second passage part 82 of the hub coupling part 31 (refer also to FIG. 7D). In this case, by the branch pipe part 23 being engaged with the second passage part 82, the hub 16 is regulated from moving to the leading end side with respect to the hub coupling part 31. As a result, the coupled state of the hub coupling part 31 (the second pipe part 63) and the hub 16 can be held. Further, the branch pipe part 23 is inhibited from entering into the first passage part 81 from the second passage part 82 by the protrusion 84. Thus, the engaged state of the branch pipe part 23 with the second passage part 82 can be held (refer to FIG. 7D).

In the state in which the hub 16 is housed inside the second body 52, the base end side of the hub 16 is caused to enter the recessed part 95 of the movable member 86, and the base end surface of the cap 19 is caused to be in contact with the partition plate part 88 of the movable member 86. More specifically, in the state in which the hub 16 is housed inside the second body 52 (in other words, in the state in which the branch pipe part 23 is engaged with the second passage part 82), the movable member 86 is caused to be pressed further to the base end side (the depth side inside the second body 52) than the initial position, by the base end surface of the hub 16. In this case, the coil spring 90 that is compressed as a result of this pressing, urges the movable member 86 and thus the hub 16, toward the leading end side. Therefore, due to the urging force, the branch pipe part 23 of the hub 16 is pressed against the second passage part 82. In this case, the branch pipe part 23 can be held favorably in the engaged state with respect to the second passage part 82, and thus, the coupled state of the hub coupling part 31 and the hub 16 can be favorably maintained.

Next, a flow when coupling the hemostatic connector 12 to the hub 16 of the sheath introducer 11 will be explained. FIGS. 7A to 7D and FIGS. 8A to 8D are explanatory diagrams illustrating the flow when coupling the hemostatic connector 12 to the hub 16. FIGS. 7A to 7D are the explanatory diagrams showing a front view. FIGS. 8A to 8D are the explanatory diagrams showing a longitudinal cross-sectional view. Further, FIGS. 7A to 7D respectively correspond to FIGS. 8A to 8D. The upward direction and the downward direction in FIGS. 7A to 7D and FIGS. 8A to 8D are, respectively, the base end side and the leading end side of the hemostatic connector 12.

Figure 8A:
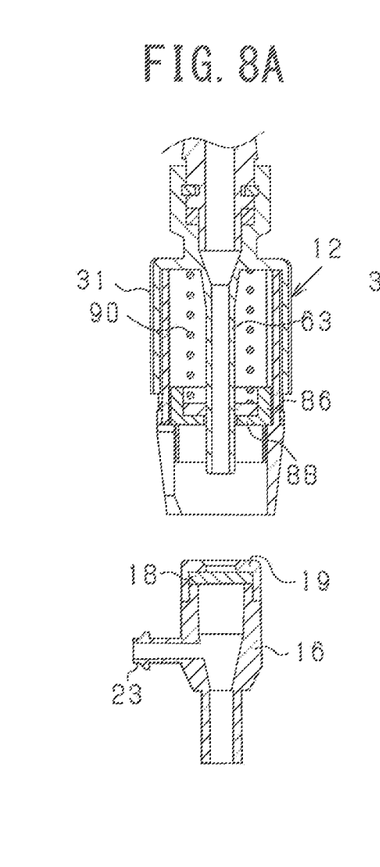
FIGS. 8A, 8B, 8C, and 8D are explanatory diagrams illustrating the flow when coupling the hemostatic connector to the hub.

As shown in FIG. 7A and FIG. 8A, the hub 16 and the hub coupling part 31 are aligned in the axial line direction in a state in which the base end surface of the hub 16 (more specifically, the cap 19) is caused to face the movable member 86 (more specifically, the partition plate part 88) of the hub coupling part 31 of the hemostatic connector 12. At this time, the branch pipe part 23 of the hub 16 and the first passage part 81 of the hub coupling part 31 are arranged in the same position in the direction around the axial line.

Figure 8B:
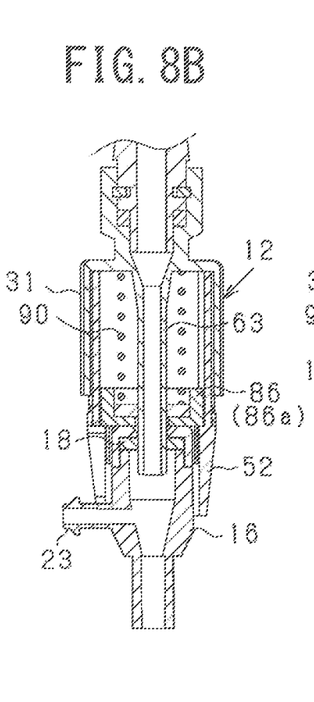
Figure 8C:
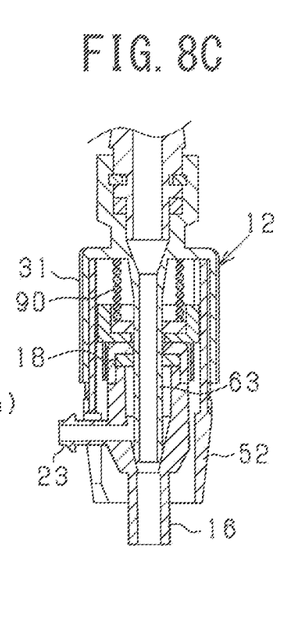
Figure 8D:
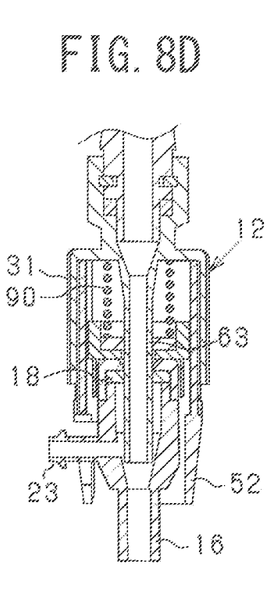

Next, as shown in FIG. 7B and FIG. 8B, the hub 16 is inserted inside the second body 52 of the hub coupling part 31. In this state, the hub 16 is pushed into the depth side (the base end side) inside the second body 52. At this time, the branch pipe part 23 of the hub 16 is caused to pass through the first passage part 81 of the hemostatic connector 12, and is guided as far as the base end part of the first passage part 81 (refer to FIG. 7C). In this way, the second pipe part 63 is pressed toward the hemostatic valve 18 of the hub 16 and penetrates the hemostatic valve 18. In this penetrated state, the second pipe part 63 is coupled to the hub 16 (refer to FIG. 8C). Further, as the hub 16 is pressed inside the second body 52, the movable member 86 inside the second body 52 is pressed by the hub 16 toward the depth side inside the second body 52, while resisting the urging force of the coil spring 90.

Next, as shown in FIG. 7D, the hub 16 is rotated to the one side (to the right side in FIG. 7D) in the direction around the axial line with respect to the hemostatic connector 12, and the branch pipe part 23 of the hub 16 is inserted into the second passage part 82. In this way, the branch pipe part 23 is engaged with the second passage part 82. As a result of this engagement, the coupled state of the second pipe part 63 with the hub 16 (the state in which the second pipe part 63 has penetrated the hemostatic valve 18) is held (refer to FIG. 8D).

Next, a flow of operations when the introduction member X is introduced into the blood vessel using the sheath introducer assembly 10 will be explained with reference to FIGS. 2A and 2B. Note that, here, the explanation will be made using a balloon catheter as an example of the introduction member X. The explanation will be made of a flow when the balloon catheter is introduced to a constricted location (a treatment target location) inside the human body. Further, the balloon catheter has a known configuration in which a balloon that can inflate and deflate using a fluid is provided on the leading end part of the balloon catheter.

At the time of the introduction operation, first, the sheath introducer 11 (more specifically, the sheath tube 15) is inserted into the blood vessel. After that, the hemostatic connector 12 is coupled to the hub 16 of the sheath introducer 11, thus forming the sheath introducer assembly 10.

Next, a guide wire G is inserted through the interior of the sheath introducer assembly 10. At this time, the guide wire G is inserted through the lumen 15a of the sheath tube 15, from the internal passage 55 of the hemostatic connector 12 through the internal passage 29 of the hub 16. Then, in the inserted state, the guide wire G is inserted into the blood vessel, and is introduced to a position beyond the constricted location inside the blood vessel.

Next, the balloon catheter is inserted through the sheath introducer assembly 10, and is introduced as far as the constricted location inside the blood vessel, while a push and pull operation is applied in the above-described inserted state. At this time, the balloon catheter is introduced along the guide wire G as far as the constricted location, while the balloon is in a deflated state. Therefore, similarly to the guide wire G, the balloon catheter is introduced into the blood vessel, through the internal passage 55 of the hemostatic connector 12, the internal passage 29 of the hub 16, and the lumen 15a of the sheath tube 15, in that order.

As shown in FIG. 6, the inner diameter of the pipe bore 64 is larger than the diameter of the lumen 15a of the sheath tube 15. Thus, a medical catheter that is inserted through the lumen 15a of the sheath tube 15 can be inserted through the internal passage 55 of the hemostatic connector 12. In other words, the hemostatic connector 12 is configured such that a medical catheter that a user wishes to insert through the sheath tube 15 can be inserted. As a result, a failure does not arise in which the medical catheter that the user wishes to insert through the sheath tube 15 does not pass through the hemostatic connector 12.

At the time of the introduction, the balloon catheter is introduced into the blood vessel in a state in which the balloon catheter penetrates (is inserted through) the slit of the hemostatic valve 38 of the hemostatic connector 12. At this time, a state is obtained in which a space between the balloon catheter and the peripheral surface of the internal passage 55 of the hemostatic connector 12 is blocked by the hemostatic valve 38. In other words, when the balloon catheter is inserted through the internal passage 55, the hemostatic valve 38 blocks a gap between the peripheral surface of the internal passage 55 and the balloon catheter. In this way, when introducing the balloon catheter into the blood vessel, blood stoppage can be performed. Specifically, in this case, when introducing the balloon catheter into the blood vessel, rather than using the hemostatic valve 18 inside the sheath introducer 11 (more specifically, inside the hub 16), the blood stoppage can be performed using the hemostatic valve 38 of the hemostatic connector 12, which has a higher hemostatic performance than the hemostatic valve 18. In this way, when introducing the balloon catheter into the blood vessel, the leakage of blood can be suppressed.

After the balloon catheter (the balloon) has been introduced to the constricted location, the balloon is inflated, thus expanding the constricted location. After that, the balloon is put into a deflated state, and the balloon catheter is withdrawn from inside the blood vessel through the inside of the sheath introducer assembly 10.

According to the above-described configuration of the present embodiment, the following effects may be obtained, for example.

The hemostatic connector 12 is configured by the Y connector part 30, which includes the hemostatic valve 38, and the hub coupling part 31 (the second pipe part 63), which is coupled to the hub 16, being inseparably integrated with each other. Therefore, the coupling operation that is performed when introducing the introduction member X (the balloon catheter) into the blood vessel is simply the operation of coupling the hub coupling part 31 (the hemostatic connector 12) to the hub 16. As a result, when introducing the introduction member X into the blood vessel, the introduction operation may be favorably performed.

The hub coupling part 31 is attached to the Y connector part 30 such that the hub coupling part 31 can rotate around the axial line of the second pipe part 63. Thus, in the state in which the second pipe part 63 is coupled to the hub 16, the Y connector part 30 can be rotated with respect to the hub 16. In this case, in the state in which the sheath introducer 11 has been introduced into the human body, the Y connector part 30 only may be rotated. As a result, the hemostatic connector 12 may be more easily handled.

The hemostatic connector 12 is configured by attaching the hub coupling part 31 to the Y connector part 30 that is the structural member of the Y connector. In this case, the hemostatic connector 12 may be manufactured using the common structural member of the Y connector (the Y connector part 30), and thus, manufacturing cost reduction and the like may be achieved.

Further, the hub coupling part 31 is attached to the leading end part of the Y connector part 30 in place of the rotator. Thus, in comparison to the general Y connector that is provided with the rotator, since the rotator is not provided, the length of the coupling portion may be shortened. Thus, a favorable configuration may be obtained in terms of securing an effective length of the sheath introducer assembly 10.

The movable member 86 (and the seal member 98) are provided in the interior of the second body 52 so as to face the base end surface of the hub 16, and the coil spring 90 is installed further to the base end side than the movable member 86. In this case, the hub 16 is urged to the leading end side by the coil spring 90, via the movable member 86. As a result, the urging force of the coil spring 90 may act on the whole region of the base end surface of the hub 16. Thus, it may be possible to suppress the occurrence of a failure resulting from tilting of the hub 16 due to the urging force acting partially on the base end surface of the hub 16.

In addition, the seal member 98 is provided overlapping with the movable member 86 (the partition plate part 88), and the hole 99, through which the second pipe part 63 is inserted, is formed in the seal member 98. Then, the inner peripheral surface of the hole 99 is caused to be in close contact with the outer peripheral surface of the second pipe part 63. In this case, even if there is a leakage of blood to the base end side from the internal passage 29 of the hub 16, for example, the blood may be suppressed from entering into the coil spring 90 side through the hole 99. In this way, the blood may be suppressed from attaching to the coil spring 90 and causing a reduction in the urging force of the coil spring 90, and thus, the above-described effects obtained as a result of the urging force may be reliably deployed.

Since the seal member 98 is disposed on the base end side surface of the partition plate part 88 of the movable member 86, it may be possible to inhibit the seal member 98 from falling out to the leading end side from the interior of the second body 52. Further, since the seal member 98 is disposed in the state of being pressed against the partition plate part 88 by the urging force of the coil spring 90, even if the seal member 98 is not fixed to the partition plate part 88 using an adhesive or the like, the seal member 98 may be installed on the partition plate part 88 in a stable state.

In addition, in the state in which the seal member 98 is pressed by the urging force of the coil spring 90, the seal member 98 is compressed in the thickness direction. As a result of that compression, it is conceivable that the hole diameter of the hole 99 may become smaller. Therefore, in this case, the effect of the close contact of the inner peripheral surface of the hole 99 with the outer peripheral surface of the second pipe part 63 may be increased, and thus, the blood may be even more reliably suppressed from entering into the coil spring 90 side through the hole 99.

It should be noted that, in terms of obtaining each of the above-described effects due to the movable member 86 and the seal member 98, the Y connector part 30 and the hub coupling part 31 need not necessarily be inseparably integrated with each other. For example, even with a configuration in which a hub coupling part is detachably coupled with another connector (the Y connector, for example) that has the hemostatic function, as long as that hub coupling part is provided with the movable member 86 and the seal member 98, the above-described effects can be obtained.

Since the end surface 63*a* on the leading end side of the second pipe part 63 forms the curved surface shape that projects toward the leading end side, when performing the coupling by inserting the second pipe part 63 through the hemostatic valve 18 of the hub 16, it may be possible to suppress the occurrence of a failure due to damaging the hemostatic valve 18. Note that, in terms of obtaining this effect, the Y connector part 30 and the hub coupling part 31 (the second pipe part 63) need not necessarily be inseparably integrated with each other, and this effect can be obtained as long as the configuration includes the second pipe part 63.

The present disclosure is not limited to the above-described embodiment, and may be embodied in the following ways, for example.

(1) In the above-described embodiment, the coupled state of the hub coupling part 31 (the second pipe part 63) and the hub 16 is held by engaging the second passage part 82 of the guide passage 80 with the branch pipe part 23 of the hub 16. However, the configuration of holding means is not limited to that configuration. For example, an engagement member (a curved hook member, for example) that can be engaged with the branch pipe part 23 may be provided on the hub coupling part 31, as the holding means, and the coupled state of the hub coupling part 31 and the hub 16 may be held by the engagement with the engagement member. Further, a pair of clamping members that can clamp the branch pipe part 23 may be provided on the hub coupling part 31 as the holding means, and the coupled state of the hub coupling part 31 and the hub 16 may be held by the clamping of the branch pipe part 23 by the clamping members.

Alternatively, the holding means need not necessarily be provided on the hub coupling part 31. In the state in which the coupling is performed by the second pipe part 63 penetrating the hemostatic valve 18 (the slit) of the hub 16, the inner peripheral surface of the slit of the hemostatic valve 18 is in close contact with the outer peripheral surface of the second pipe part 63. In this case also, the slipping out of the second pipe part 63 from the hemostatic valve 18 can be suppressed to a certain extent, and the coupled state of the hub coupling part 31 (the second pipe part 63) and the hub 16 can be maintained.

(2) In the above-described embodiment, the seal member 98 is provided on the base end side surface of the partition plate part 88 of the movable member 86. However, this may be changed, and the seal member 98 may be provided on the leading end side surface of the partition plate part 88. In this case, for example, the seal member 98 is fixed to the partition plate part 88 using an adhesive or the like.

Further, a seal member need not necessarily be the circular plate shape, and may be annular (ring-shaped), for example. In this case, for example, the hole 89 of the partition plate part 88 is formed to be somewhat larger than the outer diameter of the second pipe part 63, and the annular seal member is fitted into the hole 89. With this configuration, the second pipe part 63 is inserted through the inside of the seal member, and the inner peripheral surface of the seal member and the outer peripheral surface of the second pipe part 63 are caused to be in close contact with each other. Note that the seal member need not necessarily be provided on the movable member 86.

Further, in the above-described embodiment, the hole 89 of the partition plate part 88 and the hole 99 of the seal member 98 configure the hole through which the second pipe part 63 can be inserted. However, the hole through which the second pipe part 63 can be inserted may be configured by the hole 99 of the seal member 98 only. In this case, for example, a seal member having a thickness that corresponds to a length from the base end to the leading end of the movable member 86 may be fitted inside the movable member 86. In this case, the movable member 86 need not be provided with the partition plate part 88, and may be configured by the cylindrical part 87 only.

(3) In the above-described embodiment, the leading end surface 63a of the second pipe part 63 forms the curved surface shape that projects to the leading end side, but this may be changed. For example, it is conceivable that the leading end surface 63a of the second pipe part 63 may be a flat surface shape, or the leading end part of the second pipe part 63 may be a sharp end that is pointed toward the leading end side.

(4) In the above-described embodiment, by using the O ring 46 as the locking member, the Y connector part 30 and the hub coupling part 31 are inseparably integrated with each other. However, the configuration for inseparably integrating the Y connector part 30 and the hub coupling part 31 with each other is not limited to this example. For example, the Y connector part 30 and the hub coupling part 31 may be inseparably integrated with each other by fixing the main pipe part 33 of the Y connector part 30 (the main body part 32) to the first pipe part 62 of the hub coupling part 31 using an adhesive or the like.

Further, the main body part 32 of the Y connector part 30 and the first body 51 (the second pipe part 63) of the hub coupling part 31 may be integrally formed with each other. In this case also, a Y connector part and a hub coupling part (the second pipe part 63) can be configured to be inseparable.

(5) In the above-described embodiment, the Y connector part 30 that includes the main pipe part 33 and the branch pipe part 34 is used as the connector main body part. However, for example, a straight pipe-shaped connector that does not include a branch pipe part may be used as the main body part. Further, a connector that includes two or more branch pipe parts may be used as the connector main body part. In other words, as long as the connector main body part internally includes a hemostatic valve (a hemostatic member), the form thereof may be freely selected.

(6) In the above-described embodiment, the leading end part of the main pipe part 33 and the base end part of the first pipe part 62 are inseparably joined together. However, another member, such as a flexible tube or the like, may be provided between the leading end part of the main pipe part 33 and the base end part of the first pipe part 62. In this case, for example, one end of the tube may be inseparably joined to the leading end part of the main pipe part 33, and the other end of the tube may be inseparably joined to the base end part of the first pipe part 62.

(7) As the guide wire when introducing the sheath introducer assembly 10 into the blood vessel, there is a case in which a guide wire having a leading end part that is curved into a predetermined shape is used. Here, when this type of the guide wire is inserted through the sheath introducer assembly 10, a tubular member may be used in order to guide the guide wire into the hemostatic connector 12. More specifically, the tubular member may be used that has an outer diameter smaller than the inner diameter of the pipe bore 64, that has an inner diameter through which the guide wire can be inserted, and that has a length that extends at least as far as the base end of the second pipe part 63 from the base end of the hemostatic connector 12. In this case, for example, the user inserts the leading end of the guide wire into the tubular member and pushes the guide wire along the tubular member. The guide wire is flexible. Thus, the leading end part of the guide wire is contained inside the tubular member in a state of being extended in a substantially straight line. At this time, the user causes the leading end part of the guide wire to be contained inside the tubular member. In the state in which the leading end part of the guide wire is contained inside the tubular member, the user inserts the tubular member toward the second pipe part 63 from the base end side of the hemostatic connector 12. In a state in which the leading end of the tubular member is positioned in the vicinity of the base end of the second pipe part 63, the user pushes the guide wire toward the sheath tube 15, thus introducing the guide wire as far as a predetermined position inside the blood vessel. In this way, even when the guide wire has a curved leading end part, by using the tubular member, the user can easily insert the guide wire into the hemostatic connector 12.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:
1. A hemostatic connector comprising:
 an insertion hole configured such that an introduction member that is introduced into a human body is inserted through the insertion hole;
 a hemostatic member configured to block a gap between a peripheral surface of the insertion hole and the introduction member;

a connector main body part in which the hemostatic member is provided, the connector main body part configuring a first passage that is a portion of the insertion hole;

a coupling pipe part configured to be coupled to a hub of a sheath introducer, the coupling pipe part configuring a second passage that is a portion of the insertion hole different to the first passage; and a housing cylindrical part internally housing the hub coupled to the coupling pipe part, wherein:

the coupling pipe part is configured to be inserted into an internal hole of the hub from a base end side of the hub, the coupling pipe part being configured to be coupled to the hub in a state in which the coupling pipe part penetrates a hemostatic valve provided in the internal hole when the coupling pipe part is inserted into the internal hole, the connector main body part and the coupling pipe part are configured to be inseparable, a branch pipe passage is formed in the housing cylindrical part such that a branch pipe part that protrudes from an outer peripheral surface of the hub is caused to be passed through the branch pipe passage when coupling the coupling pipe part to the hub, a portion of the branch pipe passage is an engagement passage part that extends in a peripheral direction of the housing cylindrical part, the engagement passage part being configured to engage with the branch pipe part by the branch pipe part of the hub coupled to the coupling pipe part being inserted into the engagement passage part, an urging member is provided in an interior of the housing cylindrical part, the urging member urging the hub toward a leading end side in a state in which the branch pipe part is engaged with the engagement passage part, the leading end side being an opposite side of the base end side, a facing member is provided in the interior of the housing cylindrical part, the facing member facing a base end surface of the hub housed in the housing cylindrical part, the facing member includes a hole configured such that the coupling pipe part is inserted through the hole, the facing member being configured to move along the coupling pipe part inserted through the hole, the urging member is provided on the base end side of the facing member, the urging member urging the hub to the leading end side via the facing member, the facing member includes an elastic seal part configuring at least a part of the hole, an inner peripheral surface of a portion of the hole configured by the elastic seal part is in close contact with an outer peripheral surface of the coupling pipe part inserted through the hole, the facing member includes a facing plate part that is provided facing the base end surface of the hub, and the elastic seal part that is plate-shaped and is provided on the base end surface side of the facing plate part, and the elastic seal part is disposed in a state of being pressed against the facing plate part due to an urging force of the urging member.

2. The hemostatic connector according to claim 1, further comprising:

a hub coupling part inseparably attached to a leading end side of the connector main body part and including the coupling pipe part, the leading end side being an opposite side of the base end side, wherein the hub coupling part is attached so as to rotate with respect to the connector main body part around an axial line of the coupling pipe part in a state in which the hub coupling part is attached to the leading end side of the connector main body part.

3. The hemostatic connector according to claim 2, wherein the connector main body part is a Y connector main body part that is a structural member for configuring a Y connector, and the hub coupling part is inseparably attached to an end part on the leading end side of the Y connector main body part.

4. The hemostatic connector according to claim 1, wherein an end surface on a leading end side of the coupling pipe part is a curved surface shape that projects toward the leading end side, the leading end side being an opposite side of the base end side.

* * * * *